United States Patent [19]

Fujimori et al.

[11] Patent Number: 4,625,236
[45] Date of Patent: Nov. 25, 1986

[54] LIGHT SOURCE MEANS FOR ENDOSCOPE EMPLOYING SOLID STATE IMAGING DEVICE

[75] Inventors: Hiroyoshi Fujimori, Hachioji; Tatsuo Nagasaki, Musashino; Tadashi Kato; Masahiko Sasaki, both of Hachioji, all of Japan

[73] Assignee: Olympus Optical Co., Ltd., Tokyo, Japan

[21] Appl. No.: 755,763

[22] Filed: Jul. 17, 1985

[30] Foreign Application Priority Data

Jul. 31, 1984 [JP] Japan .................................. 59-162522

[51] Int. Cl.⁴ ............................ A61B 1/04; A61B 1/06
[52] U.S. Cl. ........................................... 358/98; 128/6; 358/42
[58] Field of Search ........................ 358/98, 42; 128/6

[56] References Cited

U.S. PATENT DOCUMENTS 4,261,344 4/1981 Moore .................................... 358/98
4,546,379 10/1985 Sarofeen ................................ 358/42
4,562,831 1/1986 Murakoshi ............................. 128/6

FOREIGN PATENT DOCUMENTS 108239 8/1978 Japan .
40408 3/1982 Japan .

*Primary Examiner*—Howard W. Britton
*Attorney, Agent, or Firm*—Armstrong, Nikaido, Marmelstein & Kubovcik

[57] ABSTRACT

A light source for an endoscope is disclosed for illuminating a subject, the image from the subject being received through a leading end of the endoscope, and being projected by an objective lens onto a solid state imaging device. Light from a light source lamp is projected onto the subject sequentially with the light transmitted through three color transmitting filters. A reflector is provided to reflect light from the light source lamp in a parallel light beam. A convex lens system for converging the parallel light from the reflector. Light from said source lamp is transmitted through a light guide to the subject. A first and second lens systems are positioned between the input end of the light guide and the convex lens system for converging the light onto the input end of the light guide. The light guide is disposed within an insert member of said endoscope. The lens systems reduce the sectional area of the light beam and restrict the included angle of the light beam. A rotary color filter is provided in said light beam and includes interference filters having high heat resistance for passing light of only a specific wavelength, to provide different colors of illuminating light to the subject.

5 Claims, 8 Drawing Figures

LIGHT SOURCE MEANS FOR ENDOSCOPE EMPLOYING SOLID STATE IMAGING DEVICE

FIELD OF THE INVENTION AND RELATED ART STATEMENT

This invention relates to an endoscope having a light source means employing an interference filter, the endoscope having a solid state imaging device.

Recently, solid state imaging devices (SID's) have been popularly used as receiving means for television cameras, endoscopes, etc.

Existing endoscopes employ optical fibers as image transmitting means and illuminating light transmitting means. The optical fibers are used in compact bundles having a large number of fibers, perhaps several tens of thousands, each fiber having a diameter of tens of microns and used as image guides and light guides, respectively. Especially, an endoscope is designed so that the image reflected from a subject is received by the focussing optical system, equipped at the leading tip of the body of an endoscope. The image is then transmitted down an image guide to the handling member on the trailing end of said image guide in order to be observed through the eyepiece of the endoscope.

In such an endoscope which employs a solid state imaging device, in order for improved diagnosis of a condition, it is helpful to receive a color image for observation.

The most popular means for receiving a color image, employs a combination of a color separation optical system and a plurality of monochromatic solid state imaging devices or solid state imaging devices attached with red, green and blue filters on the pick-up plane in mosaic arrangement.

In the former type, however, it is difficult to incorporate a color separation optical system and a plurality of solid state imaging devices in a thin and small space such as the insert member of an endoscope. As for the latter type, since the split color components are received on the imaging device separately, each one-third of the solid state imaging device should be allotted for each color component so that the resolution of pick-up elements is reduced as compared with monochromatic images.

In addition, in the latter type, since the elements for receiving each color component differ with each other, proper color registration cannot be easily achieved by mixing the color components. For such reasons, conventional systems have suggested that filters be provided through the illuminating means for illuminating successively the subject with each primary color (wave length) as shown in FIG. 1.

In FIG. 1, substantially natural light issued from light source 51 is reflected by a concave mirror 52 as a beam of substantially parallel light. The beam of light is filtered through rotary color filter 53 attached midway to condensor lens 54 to split the light into a color component to be propagated to said condensor lens 54. The split light is converged through said lens to illuminate the input end of light guide 55. The subject is illuminated by the light emitted from the output end of light guide 55.

Rotary filter 53 separates a circular disk into 3 sectors, each having with a color filter, and it is rotated by driving motor 56. The electrical signals for each image received from each illuminating each color are displayed polychromatically as color signals.

In the above-mentioned prior art, absorption filters or heat resistant interference filters may be employed in rotary filter 53 but the larger size of rotary filter requires high mechanical strength and a large capacity driving motor 6, thereby increasing the costs, enlarging the structures and increasing the weight.

On the other hand, the area illuminated by light can be reduced and the area of rotary filter 53 can be reduced by inserting rotary filter 53 into a position between condensor lens 54 and the input end of light guide 55 as shown in FIG. 2. Thus, the filter positioned in an area of converging light can be driven by means of driving motor 56 with a small torque.

In such a case, however, if absorption filters are employed as rotary filter 53 the low heat resistance of the filters causes the filters to deteriorate and become unusable very quickly. If highly heat resistant interference filters are employed, the light is incident on said filters at larger incident angles, thereby shifting the transmitted light to a shorter wave length as a whole. Accordingly, the reproducibility of color on a color display is not true, thus degraded of the fidelity of the color reproduction and seriously impairing diagnosis of subject. Prior art as disclosed, for example in Japanese Published Utility Model Application No. 40408/1982 has similar disadvantages.

OBJECT AND SUMMARY OF THE INVENTION

It is thus an object of this invention to provide a light source means with high color reproducibility for an endoscope employing solid state imaging devices.

It is another object of this invention to provide a light source means for an endoscope employing solid state imaging devices at a lower cost.

It is still another object of this invention to provide a light source means capable of optimizing the quantity of illuminating light for observation in an endoscope equipped with a solid state imaging device.

According to this invention, illuminating means of sequential color shifting type are designed to provide two sets of lens systems for reducing the divergent area of light flux at the incident end of a light guide transmitting light to a subject. In addition, a convex lens provides for converging and irradiating the light from the light source, and highly heat-resistant interference filters are at a position to filter a substantially parallel flux of light.

BRIEF DESCRIPTION OF THE DRAWINGS

FIGS. 3 to 4 relate a first embodiment of the instant invention wherein FIG. 3 is a schematic view illustrating the structure of an endoscope according to a first emdbodiment and FIG. 4 is a front view of a rotary filter.

DETAILED DESCRIPTION OF THE PREFERRED EMBODIMENTS

Figure 1:
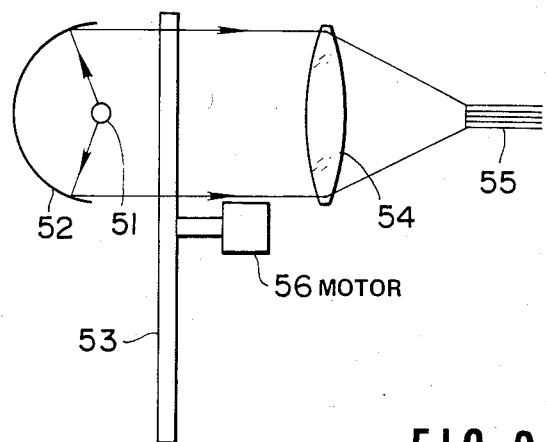
FIG. 1 is a schemtic view of an optical system in the light source means of a previously known endoscope.
Figure 2:
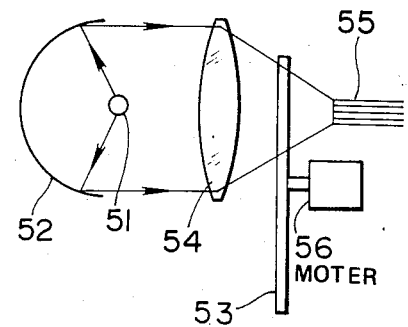
FIG. 2 is a schematic view of an optical system in the light source means of another previously known endoscope.
Figure 3:
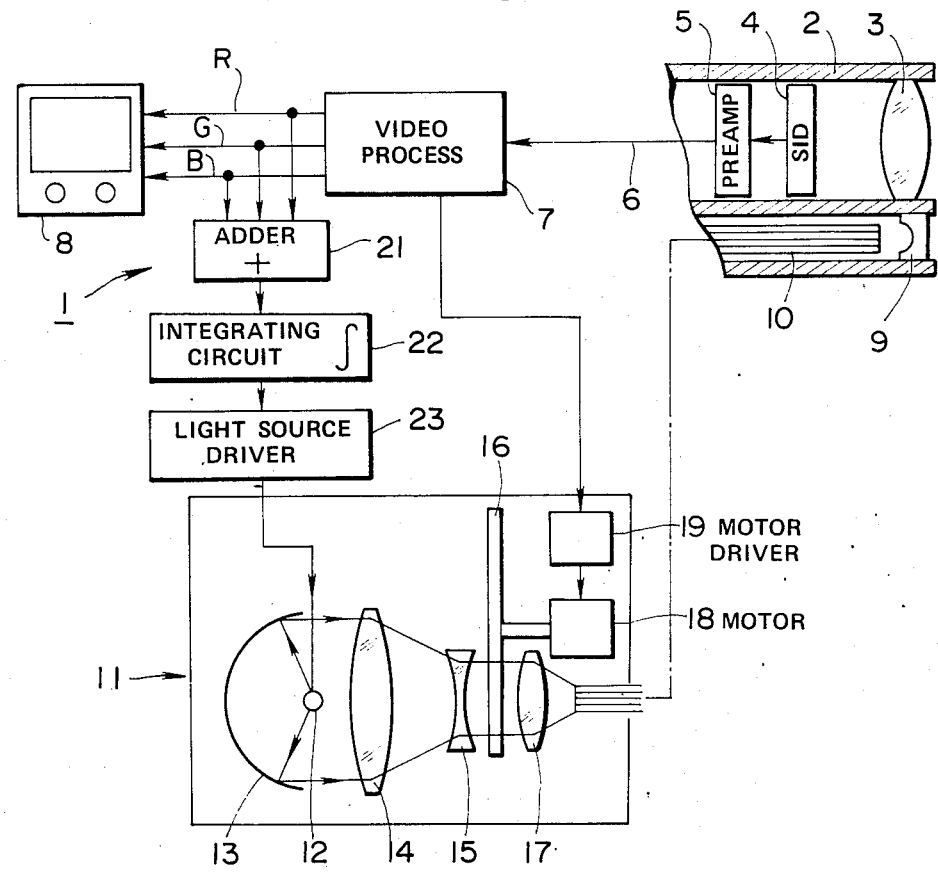

As shown in FIG. 3, endoscope 1 according to the first embodiment is provided with focussing lens 3 at the leading tip of insert member 2 and solid state imaging device (SID) 4, such as CCD (charge-coupled device) or the like so that the imaging plane coincides with the focussing plane of said objective lens 3. A great number of receiver elements having photoelectric conversion ability are arranged regularly on the imaging plane of said state imaging device 4. Each receiver element receives each split picture element to issue a photoelectrically converted electrical signal correspondent to each picture element, which is read successively by a clock signal (not shown). The read signal is amplified through preamplifier 5 with a low noise factor and put into video process member 7 through signal cable 6. Said video process member A/D converts the input signal and each monochromatic image provided by the sequential illumination by monochromatic light as will be referred to later, is changed over through a multiplexer to be recorded into each exclusive frame memory. During the reading mode, the recorded signals (data) are read, converted through D/A converter into color signals R, B and B in analog amounts, amplified, added with horizontal and vertical synchronous signals (not shown) and sent to a color television monitor 8 to be displayed as a color image.

With insert member 2, light-distributor lens 9 is incorporated in proximal relationship with objective lens 3 and light guide 10 is inserted so that the output end thereof is positioned within said distributor lens 9. The trailing end of the handle member, i.e., the incident, or input, end of said light guide 10 is attached detachably to light source means 11 according to the first embodiment.

Within said light source means 11, the illuminating light emitted from light source lamp 12 is reflected by reflector 13 having a concave or parabolic surface to reflect substantially parallel light therefrom. The substantially parallel light is converged by a first convex lens system 14 and passes through concave lens system 15 having a smaller aperture and becomes substantially parallel light once again. Said substantially parallel light is then passed through rotary filter 16, converged again through second converging convex lens system 17 and then projected through light guide 10 having an input end face thereof near the focal plane of said lens system 17. In addition, said rotary filter 16 positioned in the optical path between said concave lens sytem 15 and said convex lens system 17. The illuminating light which is transmitted to the input end of light guide 10 at the predetermined maximum incident angle is transmitted through the core member of optical fibers by total internal reflection by the boundary surface between said core and peripheral claded layer and projected on the subject directly or after the divergence through distributor lens 9. Such divergently emitted light can uniformly illuminate the focal range of objective lens 3.

Figure 4:
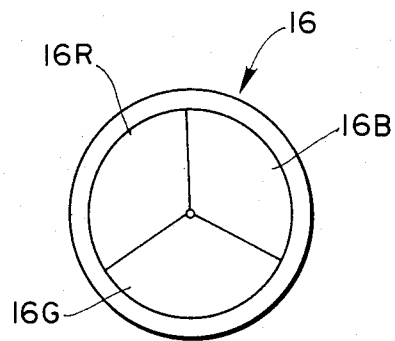

As shown in FIG. 4, the rotary filter is composed of red transmitting filter 16R, green transmitting filter 16G and blue transmitting filter 16B. Each filter exclusively transmits light having wave length of red, green or blue. Each color filter forms a sector having an angle of 120° and the rotary filter 16 is driven by motor 18 for rotation thereof.

Motor 18 is driven by the power supplied through motor driving circuit 19. It is, for example, a pulse motor rotating by a predetermined angle by the input pulse and designed so that the driving pulse is not applied to (pulse) motor 17 for a predetermined short time when each color filter 16R, 16G or 16B is positioned in the optical path between concave lens 15 and convex lens 17 and then is applied to the motor after the expiration of such a predetermined time to shift quickly the filter to the subsequent color filter. Thus the color illuminating means can sequentially illuminate the subject with 3 colors through the three color filters 16R, 16G and 16B.

The driving pulse for said motor driving circuit 19 is issued by the controlling signal supplied from video process member 7.

Color filters 16R, 16G and 16B for said rotary filter 16 are composed of interference filters (vacuum deposited film filters), each prepared by laminating a number of transparent dielectric films, depending on its purposes, on a glass substrate by vacuum deposition or the like. Thus, the filters exclusively pass light having special wave lengths utilizing the interference of light through the films. Since such an interference filter has high heat resistance, and it can be employed in zones having a high energy density of light, such as the converged parallel light as in the first embodiment.

In addition, the first embodiment is provided with automatic light controlling means for preventing a shortcoming when a subject positioned at a close distance receives exccessive dosage of illuminating light or when high-light portions having high reflection are present on a subject. The excessive dosage in such a situation may form blooming or whitish tones such that sufficient contrast is not present as well as other shortcomings are prevented by the automatic light controlling means.

Color signals R, G, B issued from video process member 7 are added through adder 21 to form brightness signal components. The brightness signal components are integrated through integrating circuit 22 having a time constant of about one frame period to be applied to the controlling terminal of light source driver 23. Light source driver 23 then provides a light controlling signal to control the luminous intensity of light source lamp 12 (i.e. illuminating intensity) and in turn emitted from the leading tip of light guide 10.

Said light source driver 23 can employ a power amplifier circuit or the like which variably controls the output current or output voltage so that the output is reduced with the increased bias level applied to the controlling terminal of driver 23.

The operation of the first embodiment having the above-mentioned mechanism will now be set forth. When the leading tip of insert member 2 in endoscope 1 is brough near a subject such as diseased organ or kept away from the subject for ascertaining an overall view, the light intensity incident to the subject is varied in accordance with the distance to the subject so that the optimum illuminating intensity is varied. The signals corresponding to each picture element issued from solid state imaging device 4 under such a condition, are input video process member 7 and recorded in each frame memory, with one frame for each color. When the subject is illuminated and the image recorded subsequently with each of the three colors, the data in each frame memory are read out concurrently, converted from digital to analog signals to represent color signals R, G, B to be displayed on color television monitor 8 as a color image, and are also put into adder 21 to enable the automatic light controlling means.

The signals are then converted into a brightness signal through adder 21, and into a light intensity controlling signal from integrating circuit 22 for controlling the output from light source driver 23 depending on the level of said controlling signal. In short, if the illuminating light intensity is excessively high to increase the level of the controlling signal, then the output from light source driver 23 is reduced and if the illuminating light intensity is excessively low to decrease the level of controlling signal, so that the illuminating intensity from light source lamp 12 is controlled to an appropriate value during the period of one frame, from one color frame to a subsequent color frame (i.e. the period of 3 frames for each color). Accordingly, the operator can save time of adjusting the illuminating light strength and devotes his attention entirely to the diagnosis or medical treatment.

Furthermore, in the first embodiment, the sequential color illuminating means comprises converging the illuminating light through first convex lens system 14, forming parallel light having a smaller sectional area through concave lens system 15 and passing the parallel light through rotary filter 16 comprising heat resistant interference filters so that the light source means can prevent incomplete spectrum of illuminating light as in the prior art. A rotary filter having a smaller size can then be employed. Thus, the torque requirement for rotating the rotary filter 16 may be reduced so that it may be driven by motor 17 with less torque. Accordingly, the light source means 11 can be miniaturized and their costs can thus be reduced. Furthermore, since the sequential color illuminating means are of a sequential type, images of a subject can be clearly displayed down to minute details without losing resolving power, thereby contributing markedly to a more accurate diagnosis.

Figure 5:
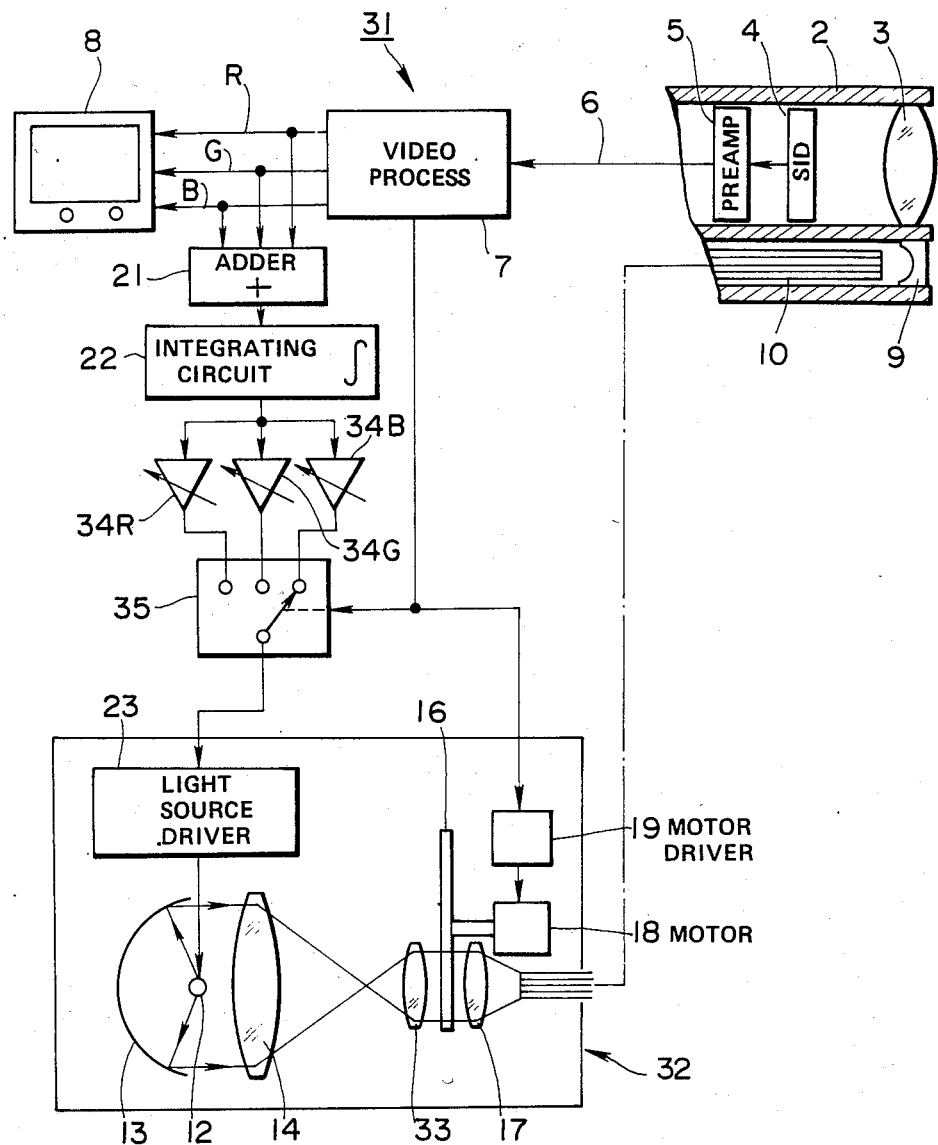
FIG. 5 is a schematic view illustrating an endoscope including a second embodiment of this invention.

FIG. 5 illustrates endoscope 31 incorrporated with a second embodiment according to the instant invention.

Light source means 32 according to the second embodiment in endoscope 31 employ convex lens system 33 in lieu of concave lens system 15 in the first embodiment.

In the second embodiment, parallel light reflected by reflector 13 is converged through first convex lens system 14 and focussed at the focal distance and then diverged and passed through convex lens system 33 arranged midway of the diverged optical path to provide substantially parallel light exiting therefrom. In short, the convex lens system 33 is arranged across the optical axis at its focal distance from the focus. Rotary filter 16 is interposed between said convex lens system 33 and second convex lens system 17 for converging the parallel light in a similar manner to the first embodiment.

On the other hand, the automatic light intensity controlling means are provided with color-complementary means. The output terminal of integrating circuit 22 is connected to each input terminal of color-complementary semi-fixed amplifiers 34R, 34G, 34B and each output terminal is connected to the controlling terminal of light source driver 23 through multiplexer 35.

Multiplexer 35 is controlled in synchronization with rotary filter 16 and connects sequentially each semi-fixed amplifier 34R, 34G or 34B with light source driver 23 in synchronization with the illumination through each color-transmitting filter 16R, 16G or 16B.

The semi-fixed amplifiers 34R, 34G, 34B act to correct the intensity distribution of the spectrum of illuminating light issued from light source lamp 12, transmitting characteristics for wave lengths of light guide 10, and photosensitive characteristics of solid state imaging device.

Otherwise, the second embodiment functions in a similar manner to the first embodiment.

The effects achieved by said second embodiment are substantially equal to those achieved by said first embodiments. The additional provision of color-complementary means can control automatically the illuminating light by correcting colors independently so that the subject can be picked up and displayed multichromatically with a higher fidelity color tone.

Figure 6:
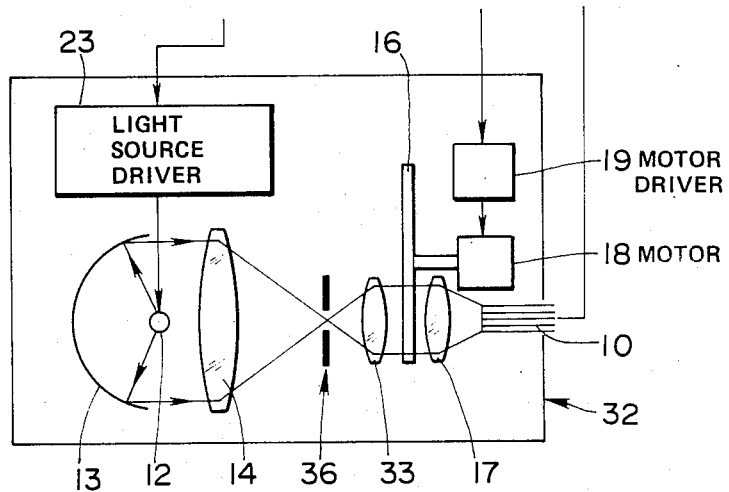
FIG. 6 is a schematic view of modification of the second embodiment according to this invention.

FIG. 6 illustrates a modification of the second embodiment.

In this modification, iris 36 is provided at the focus of the first converging convex lens system 11 to block harmful light which cannot be deflected to parallel light through convex lens system 33. In short, first convex lens system 14 having a relatively large aperture, allows for aberration of the light. Moreover, it is expensive to deflect the light to completely parallel light and the size of light source lamp 12 is also restricted. For such reasons, the light passed through convex lens system 14 cannot always focus precisely at the focus. Thus, iris 36 removes light biased comparatively largely from said focal point and the substantially focussed light is incident on convex lens system 33 for providing substantially parallel light.

As said convex lens system 33 has a smaller aperture, the system with relatively low aberration can be realized inexpensively and the light passed through said convex lens system 33 is turned to substantially parallel light. Consequently, when interference filters are employed as rotary filter 16, the incident angle is substantially 0° so as to prevent any shift of the transmitted light from the normal wave length and to provide illuminating means with high color reproducibility.

Figure 7:
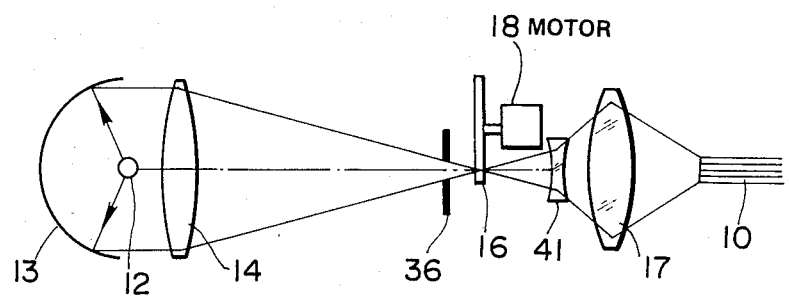
FIG. 7 is a schematic view of an optical system of a third embodiment in accordance with the instant invention.

FIG. 7 illustrates an optical system in the light source means according to the third embodiment of this invention.

In this optical system in the light source means, a convex lens system having long focal distance is employed as first converging convex lens system 14. Iris 36 removes harmful light midway, and rotary filter 16 is installed at the vicinity of focus of said convex lens system 14.

Thanks to such convex lens system 14 having longer focal distance, the maximum angle of incidence of light to the rotary filter is predetermined within a range minimizing the shift of wave length, for example, within a value of lower than 15° and by predetermining the maximum incident angle of lower than 15°, the median wave length is not substantially shifted. (For example, if the median wave length of light incident at an angle of 0° and filtered through the filter is assumed to be 1, then the median wave length of light incident at an angle of 15° is shifted from 1 to 0.99.)

After passing through said rotary filter 16, the light is diverged through concave lens system 17 to project onto the end surface of the light guide at a larger incident angle and to be emitted from the trailing end of light guide 10 as diverged illuminating light.

The third embodiment has substantially equal effects as the first embodiment and the like.

In addition, the curvature of the convex lens system can be reduced by employing a lens system having a long focal distance so that the aberration can be reduced. Moreover, interference filters having a very small area can be employed by positioning rotary filter at the focus or at the vicinity of focus of the convex lens system 14.

Figure 8:
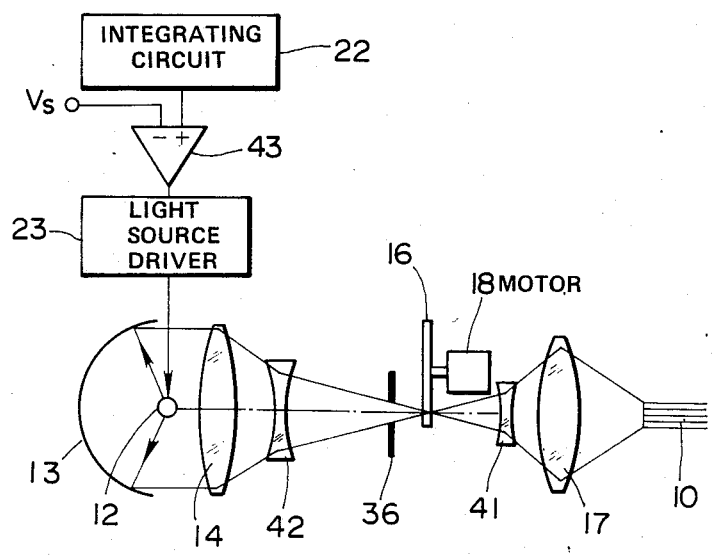
FIG. 8 is a schematic view of a fourth embodiment in accordance with the instant invention.

FIG. 8 illustrates the fourth embodiment of the instant invention.

This embodiment is designed to modify the optical system as shown in FIG. 7 by reducing the focal distance of converging convex lens system 14 to converge light within a wider range and to provide a concave lens system 42 to diverge the converged light flux through the concave lens system 42 to some extent thereby reducing sufficiently the maximum incident angle to rotary filter 16 as in said third embodiment. The length of optical system can be reduced or the outer shape of optical system can be minimized by interposing concave lens system 42 in lieu of the direct incidence of light converged through the concaves lens system 14 and through iris 36.

On the other hand, in this embodiment, the signal passed through integrating circuit 22 is applied to non-inversed input terminal of comparator 43 and the other inlet terminal is applied with reference voltage Vs.

Accordingly, the controlling signal passed through integrating circuit 22 exceeds a predetermined reference voltage Vs to issue the output from comparator 43 at a reversed or high level to nullify the driving current or voltage for light source driver 23 and to extinguish light source lamp 22.

In short, this embodiment provides illuminating light having a constant indensity but optimizes the dosage by controlling the illuminating time.

This embodiment is suitable when the intensity of emission spectrum is easily fluctuated by the change in the supplied current or the like as in light source lamp 12.

In addition, a luminous diode or the like may be employed in lieu of light source lamp 12.

It should be noticed that partial combinations of the embodiments according to this invention fall within the scope of this invention.

Additionally, many embodiments can be devised from this invention without departing from the spirit and range of this invention. Accordingly, the scope of the instant invention should be determined with respect to the following claims.

What is claimed is:

1. An endoscope comprising:
   an inserting member;
   a focusing objective lens positioned at a leading end of said inserting member, said objective lens receiving light from a subject to be examined;
   a solid state imaging device disposed in said inserting member such that an image plane of said imaging device is positioned at the focal plane of said objective lens;
   a video process means receiving an output from said solid state imaging device for recording in a memory electrical signals from said imaging device corresponding to an image focussed on the image plane of said imaging device and outputting color signals therefrom;
   display means connected to said video process means for displaying said color signals;
   a light guide disposed within said inserting members for transmitting light therethrough, said light guide having an input end and an output end thereof, said output end positioned proximal to said objective lens for illuminating said subject;
   a light source means for projecting light onto the input end of said light guide, said light source means providing sequential color illumination of three different colors to said light guide, including,
      an illuminating source lamp,
      a reflector, reflecting light from said source lamp in a parallel beam,
      a convex lens system disposed in said parallel light path for converging said parallel light, to project said converging light onto said input end of said light guide,
      a first lens system and a second lens system disposed in the optical path between said convex lens system and the input end of said light guide, said first lens system being positioned between said second lens system and said convex lens system, such that the cross sectional area of the light beam between said first and second lens systems is less than the cross sectional area of the parallel light beam between said reflector and said convex lens system, and such that said light beam between said first and second lens systems has a smaller angle with respect to the optical axis of said lens systems than the light between said convex lens system and said first lens system,
      a rotary intereference color filter rotatably disposed in the light path between said first and second lens systems, said interference color filter having three different color filters therein such that each of the different color filters are sequentially positioned in the light path during rotation for passing light having specific wavelengths therethrough, and
      driving means for rotating said rotary intereference color filter to sequentially illuminate the input end of the light guide, and in turn the subject with three colors of illuminating light.

2. The endoscope of claim 1, wherein said first lens system is concave and said second lens system is convex.

3. The endoscope of claim 1, wherein both said first and second lens system are convex.

4. The endoscope of claims 2 or 3, wherein an iris is disposed proximal to the focus point of the converging light to provide a small opening through which the focussed light may pass and to screen out unwanted light.

5. The endoscope of claim 1, further comprising an automatic light intensity conroller, including
   an adder means connected to said video process means for generating a brightness signal by adding the input color signals from said video process means;
   integrating means connected to said adder means for integrating said brightness signal for a predetermined time constant of approximately one frame period, and
   a light source driver means for receiving said integrated brightness signal and producing a controlling signal and outputting same to said source lamp for controlling the intensity of illumination thereof.

* * * * *